United States Patent
Mosnier et al.

(10) Patent No.: US 10,318,655 B2
(45) Date of Patent: Jun. 11, 2019

(54) METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT'S VERTEBRAL COLUMN

(71) Applicant: MEDICREA INTERNATIONAL, Neyron (FR)

(72) Inventors: Thomas Mosnier, Anthon (FR); David Ryan, Collonges Au Mont d'Or (FR); Vincent Fiere, Lyons (FR)

(73) Assignee: Medicrea International, Rillieux-la-Pape (FR)

( * ) Notice: Subject to any disclaimer, the term of this patent is extended or adjusted under 35 U.S.C. 154(b) by 551 days.

(21) Appl. No.: 14/914,474

(22) PCT Filed: Sep. 17, 2014

(86) PCT No.: PCT/IB2014/064586
§ 371 (c)(1),
(2) Date: Feb. 25, 2016

(87) PCT Pub. No.: WO2015/040552
PCT Pub. Date: Mar. 26, 2015

(65) Prior Publication Data
US 2016/0210374 A1 Jul. 21, 2016

(30) Foreign Application Priority Data

Sep. 18, 2013 (FR) ...................................... 13 58988

(51) Int. Cl.
*A61B 17/56* (2006.01)
*A61B 17/70* (2006.01)
(Continued)

(52) U.S. Cl.
CPC .......... *G06F 17/50* (2013.01); *A61B 17/7011* (2013.01); *A61B 34/10* (2016.02);
(Continued)

(58) Field of Classification Search
CPC ..... G06F 17/50; A61B 17/7011; A61B 34/10; A61B 2034/108; A61B 2034/105; A61B 2017/568
See application file for complete search history.

(56) References Cited

U.S. PATENT DOCUMENTS

| 5,006,984 A | 4/1991 | Steele |
| 5,163,440 A | 11/1992 | DeLuca et al. |

(Continued)

FOREIGN PATENT DOCUMENTS

| AU | 2015258176 | 12/2015 |
| AU | 2015202416 | 3/2017 |

(Continued)

OTHER PUBLICATIONS

US 9,451,972 B2, 09/2016, Lang et al. (withdrawn)
(Continued)

*Primary Examiner* — Suzanne Lo
(74) *Attorney, Agent, or Firm* — Knobbe, Martens, Olson & Bear, LLP (57) ABSTRACT

The method according the the invention comprises the following steps: a) taking a sagittal preoperative x-ray of the vertebral column of the patient to be treated, extending from the cervical vertebrae to the femoral heads; b) on that x-ray, identifying the pelvic parameters, the lumbar lordosis, the position of the apical lumbar vertebra, distances called SVA and SFD and a cloud of points; c) deducing, among predetermined morphotypes, the morphotype to which the treated vertebral column corresponds and deducing therefrom the desired postoperative apex point; d) positioning the different (Continued)

points of the cloud of points in a reference centered at the plate of S1; e) simulating the correction to be applied to the lumbar segment to be treated, by defining co-radial arcs situated below and above the desired postoperative apex point; defining two arcs concentric to the two curvatures obtained, which are tangent to each other at the apex point; f) translating these arcs away from the mean line of the vertebral column and defining a two- or three-dimensional model of the rod to be implanted, curved along the arcs.

17 Claims, 9 Drawing Sheets

(51) Int. Cl.
   *A61B 34/10*   (2016.01)
   *G06F 17/50*   (2006.01)
(52) U.S. Cl.
   CPC ... *A61B 2017/568* (2013.01); *A61B 2034/105* (2016.02); *A61B 2034/108* (2016.02)

(56) References Cited

U.S. PATENT DOCUMENTS

| | | |
|---|---|---|
| 5,224,035 A | 6/1993 | Yamashita et al. |
| 5,251,127 A | 10/1993 | Raab |
| 5,291,901 A | 3/1994 | Graf |
| 5,305,203 A | 4/1994 | Raab |
| 5,312,405 A | 5/1994 | Korotko et al. |
| 5,413,116 A | 5/1995 | Radke et al. |
| 5,514,180 A | 5/1996 | Heggeness |
| 5,667,506 A | 9/1997 | Sutterlin |
| 5,748,767 A | 5/1998 | Raab |
| 5,785,663 A | 7/1998 | Sarvazyan |
| 6,015,409 A | 1/2000 | Jackson |
| 6,213,958 B1 | 4/2001 | Winder |
| 6,282,437 B1 | 8/2001 | Franck et al. |
| 6,364,849 B1 | 4/2002 | Wilcox |
| 6,385,475 B1 | 5/2002 | Cinquin et al. |
| 6,409,684 B1 | 6/2002 | Wilk |
| 6,443,953 B1 | 9/2002 | Perra et al. |
| 6,499,488 B1 | 12/2002 | Hunter et al. |
| 6,565,519 B2 | 5/2003 | Benesh |
| 6,585,666 B2 | 7/2003 | Suh et al. |
| 6,711,432 B1 | 3/2004 | Krause et al. |
| 6,715,213 B2 | 4/2004 | Richter |
| 6,716,213 B2 | 4/2004 | Shitoto |
| 6,746,449 B2 | 6/2004 | Jones et al. |
| 6,786,930 B2 | 9/2004 | Biscup |
| 7,066,938 B2 | 6/2006 | Slivka et al. |
| 7,338,526 B2 | 3/2008 | Steinberg et al. |
| 7,509,183 B2 | 3/2009 | Lin |
| 7,534,263 B2 | 5/2009 | Burdulis |
| 7,606,613 B2 | 10/2009 | Simon et al. |
| 7,611,522 B2 | 11/2009 | Gorek |
| 7,618,451 B2 | 11/2009 | Fitz et al. |
| 7,634,119 B2 | 12/2009 | Tsougarakis et al. |
| 7,635,367 B2 | 12/2009 | Groiso |
| 7,660,623 B2 | 2/2010 | Hunter et al. |
| 7,674,293 B2 | 3/2010 | Kuiper et al. |
| 7,715,602 B2 | 5/2010 | Richard |
| 7,763,054 B2 | 7/2010 | Clement et al. |
| 7,824,413 B2 | 11/2010 | Varieur et al. |
| 7,835,778 B2 | 11/2010 | Foley et al. |
| 7,840,253 B2 | 11/2010 | Tremblay et al. |
| 7,862,593 B2 | 1/2011 | Clement et al. |
| 7,918,887 B2 | 4/2011 | Roche |
| 7,953,471 B2 | 5/2011 | Clayton et al. |
| 7,981,158 B2 | 7/2011 | Fitz et al. |
| 7,996,061 B2 | 8/2011 | Mollard et al. |
| 7,996,064 B2 | 8/2011 | Simon et al. |
| 8,000,926 B2 | 8/2011 | Roche et al. |
| 8,046,050 B2 | 10/2011 | Govari et al. |
| 8,066,708 B2 | 11/2011 | Lang et al. |
| 8,077,950 B2 | 12/2011 | Tsougarakis et al. |
| 8,083,778 B2 | 12/2011 | Clemet et al. |
| 8,105,330 B2 | 1/2012 | Fitz et al. |
| 8,142,842 B2 | 3/2012 | Nicholas et al. |
| 8,196,825 B2 | 6/2012 | Turner et al. |
| 8,211,109 B2 | 7/2012 | Groiso |
| 8,241,296 B2 | 8/2012 | Wasielewski |
| 8,246,680 B2 | 8/2012 | Betz et al. |
| 8,265,790 B2 | 9/2012 | Amiot et al. |
| 8,270,253 B1 | 9/2012 | Roche et al. |
| 8,275,594 B2 | 9/2012 | Lin et al. |
| 8,308,772 B2 | 11/2012 | Clement et al. |
| 8,308,775 B2 | 11/2012 | Clement et al. |
| 8,337,501 B2 | 12/2012 | Fitz et al. |
| 8,372,075 B2 | 2/2013 | Groiso |
| 8,377,073 B2 | 2/2013 | Wasielewski |
| 8,394,142 B2 | 3/2013 | Berg et al. |
| 8,398,681 B2 | 3/2013 | Augostino et al. |
| 8,400,312 B2 | 3/2013 | Hotokebuchi et al. |
| 8,414,592 B2 | 4/2013 | Quirno |
| 8,442,621 B2 | 5/2013 | Gorek et al. |
| 8,465,527 B2 | 6/2013 | Clement |
| 8,494,805 B2 | 7/2013 | Roche et al. |
| 8,506,632 B2 | 8/2013 | Ganem et al. |
| 8,532,806 B1 | 9/2013 | Masson |
| 8,535,337 B2 | 9/2013 | Chang et al. |
| 8,556,983 B2 | 10/2013 | Bojarski et al. |
| 8,588,892 B2 | 11/2013 | Hladio et al. |
| 8,636,776 B2 | 1/2014 | Rosenberg et al. |
| 8,672,948 B2 | 3/2014 | Lemaitre |
| 8,685,093 B2 | 4/2014 | Anderson et al. |
| 8,690,888 B2 | 4/2014 | Stein et al. |
| 8,718,820 B2 | 5/2014 | Amiot et al. |
| 8,758,357 B2 | 6/2014 | Frey |
| 8,777,877 B2 | 7/2014 | Stein et al. |
| 8,784,339 B2 | 7/2014 | Stein et al. |
| 8,801,786 B2 | 8/2014 | Bernard et al. |
| 8,814,877 B2 | 8/2014 | Wasielewski |
| 8,852,237 B2 | 10/2014 | Kalfas et al. |
| 8,855,389 B1 | 10/2014 | Hoffman et al. |
| 8,864,764 B2 | 10/2014 | Groiso |
| 8,870,889 B2 | 10/2014 | Frey |
| 8,900,316 B2 | 12/2014 | Lenz |
| 8,911,448 B2 | 12/2014 | Stein |
| 8,926,673 B2 | 1/2015 | Clement et al. |
| 8,945,133 B2 | 2/2015 | Stein et al. |
| 8,956,416 B2 | 2/2015 | McCarthy |
| 8,974,467 B2 | 3/2015 | Stone |
| 8,983,813 B2 | 3/2015 | Miles et al. |
| 8,998,962 B2 | 4/2015 | Birch |
| 9,011,448 B2 | 4/2015 | Roche et al. |
| 9,034,037 B2 | 5/2015 | Fiere et al. |
| 9,039,772 B2 | 5/2015 | Park et al. |
| 9,056,017 B2 | 6/2015 | Kotlus |
| 9,066,701 B1 | 6/2015 | Finley et al. |
| 9,066,734 B2 | 6/2015 | Schoenfeld et al. |
| 9,078,755 B2 | 7/2015 | Mahfouz |
| 9,101,492 B2 | 8/2015 | Mangione et al. |
| 9,115,998 B2 | 8/2015 | Proulx et al. |
| 9,119,572 B2 | 9/2015 | Gorek et al. |
| 9,119,671 B2 | 9/2015 | Kast |
| 9,125,680 B2 | 9/2015 | Kostrzewski et al. |
| 9,144,440 B2 | 9/2015 | Aminian |
| 9,144,470 B2 | 9/2015 | Proulx et al. |
| 9,168,153 B2 | 10/2015 | Bettenga |
| 9,173,661 B2 | 11/2015 | Metzger et al. |
| 9,180,015 B2 | 11/2015 | Fitz et al. |
| 9,192,412 B2 | 11/2015 | Meyrat et al. |
| 9,198,678 B2 | 12/2015 | Frey et al. |
| 9,232,955 B2 | 1/2016 | Bonin, Jr. et al. |
| 9,233,001 B2 | 1/2016 | Miles et al. |
| 9,237,952 B2 | 1/2016 | Kurtz |
| 9,248,023 B2 | 2/2016 | Ries et al. |
| 9,250,620 B2 | 2/2016 | Kotlus |
| 9,278,010 B2 | 3/2016 | Gibson et al. |
| 9,283,048 B2 | 3/2016 | Kostrzewski et al. |
| 9,289,221 B2 | 3/2016 | Gelaude et al. |
| 9,289,270 B2 | 3/2016 | Gielen et al. |

(56) References Cited

U.S. PATENT DOCUMENTS

| | | |
|---|---|---|
| 9,295,482 B2 | 3/2016 | Fitz et al. |
| 9,295,497 B2 | 3/2016 | Schoenfeld et al. |
| 9,295,561 B2 | 3/2016 | Ball et al. |
| 9,301,768 B2 | 4/2016 | Buza et al. |
| 9,308,050 B2 | 4/2016 | Kostrzewski et al. |
| 9,308,091 B2 | 4/2016 | Lang |
| 9,314,275 B2 | 4/2016 | Clement et al. |
| 9,314,343 B2 | 4/2016 | Parisi et al. |
| 9,320,547 B2 | 4/2016 | Augostino |
| 9,320,604 B2 | 4/2016 | Miles et al. |
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kühnel |
| 9,381,085 B2 | 7/2016 | Axelson et al. |
| 9,387,015 B2 | 7/2016 | Taylor |
| 9,392,953 B1 | 7/2016 | Gharib |
| 9,393,052 B2 | 7/2016 | Berg et al. |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,443 B2 | 9/2016 | Montello et al. |
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,023 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe et al. |
| 9,491,415 B2 | 11/2016 | Deitz et al. |
| 9,492,183 B2 | 11/2016 | Wilkinson et al. |
| 9,495,483 B2 | 11/2016 | Steines et al. |
| 9,495,509 B2 | 11/2016 | Amiot et al. |
| 9,498,260 B2 | 11/2016 | Funk et al. |
| 9,504,502 B2 | 11/2016 | Kuiper et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll |
| 9,579,043 B2 | 2/2017 | Chien et al. |
| 9,585,597 B2 | 3/2017 | MCCaullet et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agmihotri et al. |
| 9,622,712 B2 | 4/2017 | Munro et al. |
| 9,629,723 B2 | 4/2017 | Parisi et al. |
| 9,642,633 B2 | 5/2017 | Frey et al. |
| 9,649,170 B2 | 5/2017 | Park et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow |
| 9,675,471 B2 | 6/2017 | Bojarski et al. |
| 9,693,831 B2 | 7/2017 | Mosnier |
| 9,757,072 B1 | 9/2017 | Urbalejo |
| 9,782,228 B2 | 10/2017 | Mosnier et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,045,824 B2 | 8/2018 | Mosnier et al. |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0103432 A1 | 8/2002 | Kawchuk |
| 2003/0191383 A1 | 10/2003 | Ben-Haim et al. |
| 2004/0120781 A1 | 6/2004 | Luca |
| 2004/0143243 A1 | 7/2004 | Wahrburg |
| 2004/0152972 A1 | 8/2004 | Hunter |
| 2004/0167637 A1 | 8/2004 | Biscup |
| 2004/0215190 A1* | 10/2004 | Nguyen ............ A61B 17/1671 606/86 A |
| 2004/0243148 A1 | 12/2004 | Wasuekewski |
| 2004/0267279 A1 | 12/2004 | Casutt et al. |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Kaula et al. |
| 2005/0203531 A1 | 9/2005 | Lakin et al. |
| 2005/0203532 A1 | 9/2005 | Ferguson et al. |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0069324 A1 | 3/2006 | Block et al. |
| 2006/0074431 A1 | 4/2006 | Sutton et al. |
| 2006/0136058 A1 | 6/2006 | Pietrzak |
| 2006/0285991 A1 | 12/2006 | McKinley |
| 2006/0287627 A1 | 12/2006 | Johnson |
| 2007/0021682 A1 | 1/2007 | Gharib et al. |
| 2007/0118243 A1 | 5/2007 | Schroeder et al. |
| 2007/0225731 A1 | 9/2007 | Couture et al. |
| 2008/0058945 A1 | 3/2008 | Hajaj et al. |
| 2008/0079546 A1 | 4/2008 | Alicot et al. |
| 2008/0108991 A1 | 5/2008 | von Jako |
| 2008/0255575 A1 | 10/2008 | Justis et al. |
| 2009/0024164 A1 | 1/2009 | Neubardt |
| 2009/0194206 A1 | 8/2009 | Jeon et al. |
| 2009/0204159 A1 | 8/2009 | Justis et al. |
| 2009/0254326 A1 | 10/2009 | Isaacs |
| 2010/0042157 A1 | 2/2010 | Trieu |
| 2010/0100011 A1 | 4/2010 | Roche |
| 2010/0191071 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 3/2011 | Bojarski et al. |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0345718 A1 | 6/2013 | Crawford et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0303883 A1 | 11/2013 | Zehavi et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |

(56) References Cited

U.S. PATENT DOCUMENTS

| | | |
|---|---|---|
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0296860 A1 | 10/2014 | Stein et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Gharib et al. |
| 2015/0100066 A1 | 4/2015 | Kostrezewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mafhouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin |
| 2016/0038307 A1 | 2/2016 | Bettenga |
| 2016/0045230 A1 | 2/2016 | Lowery et al. |
| 2016/0045317 A1 | 2/2016 | Lang et al. |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0228192 A1 | 8/2016 | Jansen et al. |
| 2016/0235480 A1 | 8/2016 | Scholl et al. |
| 2016/0235493 A1 | 8/2016 | LeBoeuf, II et al. |
| 2016/0242857 A1 | 8/2016 | Scholl |
| 2016/0242934 A1 | 8/2016 | Van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | LaVallee et al. |
| 2016/0283676 A1 | 9/2016 | Kelly et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasiewlewski |
| 2017/0119472 A1 | 5/2017 | Herrmann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0143426 A1 | 5/2017 | Isaacs et al. |
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0245937 A1 | 8/2017 | Mosnier |
| 2017/0252107 A1 | 9/2017 | Turner et al. |
| 2018/0132942 A1 | 5/2018 | Mosnier et al. |
| 2018/0256067 A1 | 9/2018 | Chen et al. |
| 2018/0289396 A1 | 10/2018 | McGahan et al. |
| 2018/0295584 A1 | 10/2018 | Gliner et al. |
| 2018/0303552 A1 | 10/2018 | Ryan et al. |
| 2019/0046268 A1 | 2/2019 | Mosnier et al. |
| 2019/0069956 A1 | 3/2019 | Ryan et al. |

FOREIGN PATENT DOCUMENTS

| | | |
|---|---|---|
| CN | 1816134 | 8/2006 |
| CN | 102805677 | 12/2012 |
| CN | 104127229 | 11/2014 |
| CN | 205073000 | 3/2016 |
| CN | 103892953 | 5/2016 |
| CN | 104434287 | 1/2017 |
| CN | 104323843 | 7/2017 |
| CN | 105078555 | 11/2018 |
| EP | 1570781 | 7/2005 |
| EP | 2053580 | 4/2009 |
| EP | 2749235 | 7/2014 |
| EP | 2754419 | 7/2014 |
| EP | 2496183 | 9/2015 |
| EP | 3000443 | 3/2016 |
| EP | 2608749 | 8/2016 |
| EP | 2403434 | 4/2017 |
| EP | 3431032 | 1/2019 |
| FR | 1358988 | 4/1964 |
| FR | 1360208 | 5/1964 |
| JP | 2016-540610 | 12/2016 |
| WO | WO1998/55038 | 12/1998 |
| WO | WO 200053077 | 9/2000 |
| WO | WO2004017836 | 3/2004 |
| WO | WO 2004/089224 | 10/2004 |
| WO | WO 2005/074368 | 8/2005 |
| WO | WO 2006/075331 | 7/2006 |
| WO | WO 2006/084193 | 8/2006 |
| WO | WO 2007/035925 | 3/2007 |
| WO | WO 2007/038290 | 4/2007 |
| WO | WO 2008/002588 | 1/2008 |
| WO | WO2008079546 | 7/2008 |
| WO | WO 2008/124079 | 10/2008 |
| WO | WO2009119181 | 10/2009 |
| WO | WO 2010/044880 | 4/2010 |
| WO | WO 2010/064234 | 6/2010 |
| WO | WO2010/121147 | 10/2010 |
| WO | WO 2010/147972 | 12/2010 |
| WO | WO 2011/021192 | 2/2011 |
| WO | WO2012/012863 | 2/2012 |
| WO | WO 2012/131660 | 10/2012 |
| WO | WO2013/003435 | 1/2013 |
| WO | WO2016102026 | 12/2014 |
| WO | WO2015/040552 | 3/2015 |
| WO | WO2015/056131 | 4/2015 |
| WO | WO2015/079011 | 6/2015 |
| WO | WO2015/89118 | 6/2015 |
| WO | WO2015185219 | 6/2015 |
| WO | WO2016044352 | 9/2015 |
| WO | WO 2015/195843 | 12/2015 |
| WO | WO2015/200720 | 12/2015 |
| WO | WO2016088130 | 12/2015 |

(56) References Cited

FOREIGN PATENT DOCUMENTS

| WO | WO2016/019424 | 2/2016 |
|---|---|---|
| WO | WO2016/019425 | 2/2016 |
| WO | WO2016/019426 | 2/2016 |
| WO | WO2016/26053 | 2/2016 |
| WO | WO 2016/032875 | 3/2016 |
| WO | WO2016/048800 | 3/2016 |
| WO | WO 2016/012726 | 4/2016 |
| WO | WO2016/094826 | 6/2016 |
| WO | WO2017001851 | 6/2016 |
| WO | WO2016/137347 | 9/2016 |
| WO | WO2016/148675 | 9/2016 |
| WO | WO2016/165030 | 10/2016 |
| WO | WO2017/39596 | 3/2017 |
| WO | WO 2017/064719 | 4/2017 |
| WO | WO 2017/066518 | 4/2017 |
| WO | WO2017/077356 | 5/2017 |
| WO | WO2017/079655 | 5/2017 |
| WO | WO 2017/127838 | 7/2017 |
| WO | WO 2017/221257 | 12/2017 |
| WO | WO 2018/087758 | 5/2018 |
| WO | WO2018/131044 | 7/2018 |
| WO | WO2018185755 | 10/2018 |
| WO | WO 2018/193316 | 10/2018 |
| WO | WO 2018/193317 | 10/2018 |
| WO | WO201914452 | 1/2019 |

OTHER PUBLICATIONS

Aubin et al. "Preoperative Planning Simulator for Spinal Deformity Surgeries", 2008, SPINE vol. 33, No. 20. pp. 2143-2152.*
Abe et la. "Scoliosis corrective force estimation from the implanted rod deformation using 3D FEM analysis", 2015, Scoliosis 10, 6 pages.*
International Search Report in PCT Application PCT/IB2014/064586, dated Dec. 23, 2014, in 2 pages.
International Search Report in PCT Application PCT/US2016/060676, dated Nov. 5, 2017 in 7 pages.
Reinshagen et al. "A novel minimally invasive technique for lumbar decompression, realignment, and navigated interbody fusion", J Clin Neurosci. 2015, 22(9):1484-1490; XP055503028.
Rickert et Al., "Posterior lumbar interbody fusion implants", Orthopaede, Springer Verlag, Berlin, DE vol. 44, No. 2 dated Jan. 28, 2015 pp. 162-169.
Spontech Medical AG Vertaplan—die Software für Wirbelsäulenchirurgen, Aug. 29, 2013 Retrieved from the Internet: URL: https://www.youtube.com/watch?v=q0qhW1T1cp8 in 1 page.
International Search Report and Written Opinion in PCT Application PCT/IB2018/000551, dated Dec. 12, 2018 in 9 pages.

* cited by examiner

METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT'S VERTEBRAL COLUMN

CROSS REFERENCE TO RELATED APPLICATION

This application is a national stage entry of PCT/IB2014/064586 filed Sep. 17, 2014, under the International Convention claiming priority over French Patent Application No. 1358988 filed Sep. 18, 2013.

FIELD OF THE INVENTION

The present invention relates to a method making it possible to produce the ideal curvature of a rod of vertebral osteosynthesis material designed to support a patient's vertebral column.

BACKGROUND OF THE INVENTION

Figure 1:
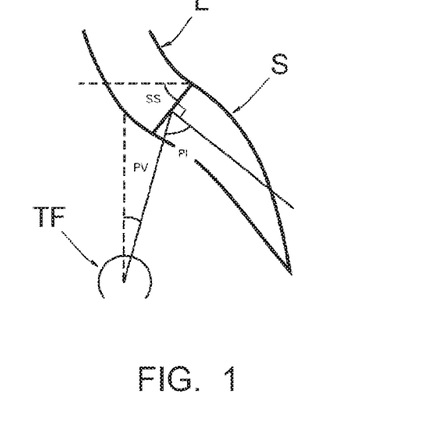
FIG. 1 very diagrammatically shows the base of the vertebral column.

It is known to analyze a patient's vertebral column in reference to so-called "pelvic" parameters and different morphotypes of a vertebral column, documented in the scientific literature. The appended FIG. 1 very diagrammatically shows the base of the vertebral column, i.e., part of the lumbar vertebrae L and the sacrum S, as well as the femoral heads TF; the aforementioned pelvic criteria are:

the SS (sacral slope) criterion, which is the incline angle of the plate of S1 (first vertebra of the sacrum), relative to the horizontal;

the PV (pelvic version) criterion, which is the angle formed by the straight segment connecting the center of the femoral heads TF and the center of the plate of S1 with the vertical;

the PI (pelvic incidence) criterion, which is the angle formed by the straight segment connecting the center of the femoral heads TF and the center of the plate of S1 with the perpendicular to the plate of S1.

Figure 2A:
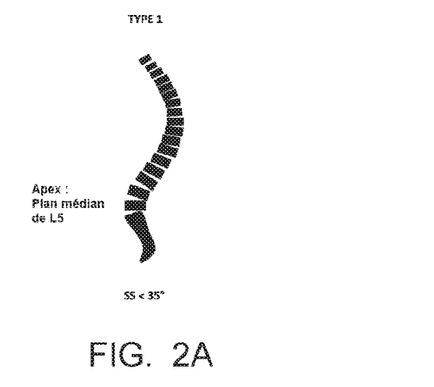
FIG. 2A shows a so-called "type 1" morphotype, in which the apex is situated at the median plane of L5 and the SS criterion corresponds to an angle smaller than 35°.
Figure 2B:
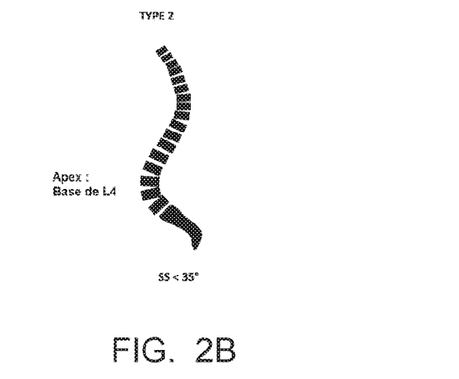
FIG. 2B shows a so-called "type 2" morphotype, in which the apex is situated at the base of L4 and the SS criterion corresponds to angle smaller than 35°.
Figure 2C:
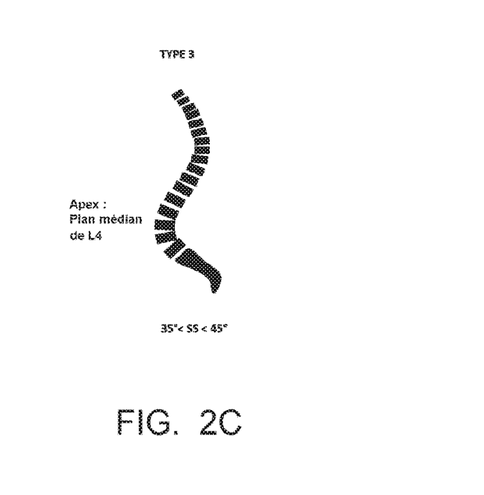
FIG. 2C shows a so-called "type 3" morphotype, in which the apex is situated at the median plane of L4 and the SS criterion corresponds to angle comprised between 35° and 45°.
Figure 2D:
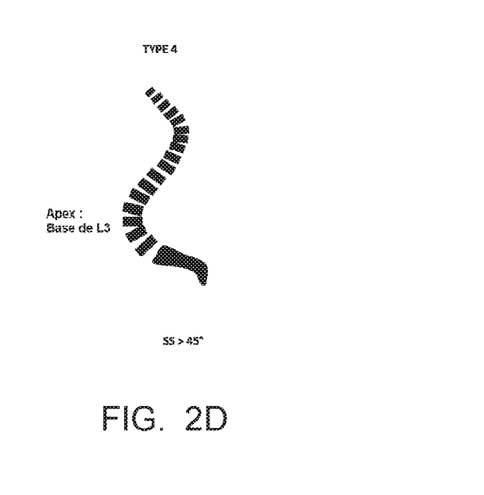
FIG. 2D shows a so-called "type 4" morphotype, in which the apex is situated at the base of L3 and the SS criterion corresponds to angle larger than 45°.

FIGS. 2A to 2D respectively show:

a so-called "type 1" morphotype, in which the apex (i.e., the forwardmost point of the vertebral column) is situated at the median plane of L5 (fifth lumbar vertebra), and the SS criterion corresponds to an angle smaller than 35°;

a so-called "type 2" morphotype, in which the apex is situated at the base of L4 (fourth lumbar vertebra), and the SS criterion corresponds to an angle smaller than 35°;

a so-called "type 3" morphotype, in which the apex is situated at the median plane of L4, and the SS criterion corresponds to an angle comprised between 35° and 45°;

a so-called "type 4" morphotype, in which the apex is situated at the base of L3 (third lumbar vertebra), and the SS criterion corresponds to an angle larger than 45°.

It is accepted that an individual will adopt a natural vertebral column posture, called "economic", avoiding pain and other pathologies, if his pelvic parameters in particular are in agreement with his back morphotype. If this is not the case, surgical treatment may be considered in order to reestablish proper posture of the vertebral column, in which that agreement exists.

It is well known to perform this type of recovery using rigid vertebral rods, in particular made of metal, fastened to the vertebrae using anchor members such as pedicle screws or laminar hooks, which rods must be curved suitably based on the correction to be done. The publication of patent application No. WO 98/55038 illustrates material of this type.

It has been shown that imparting the appropriate curvature to a straight rod may be very difficult for a surgeon, the curvature being more or less pronounced in any given location of the rod. Currently, such a curvature is done at the surgeon's discretion and calls greatly on the latter's experience and dexterity. The trial and error necessary to obtain an appropriate curvature have the significant drawback of extending the operation time, which is not desirable for the patient, and the risk of implanting a rod with a non-ideal curvature cannot be ruled out.

OBJECTS OF THE INVENTION

The present invention aims to resolve this essential drawback.

The patent application publications No. WO 2004/017836 A2, WO 2009/254326 A1 and US 2008/079546 A2 describe methods that do not achieve this goal satisfactorily.

SUMMARY OF THE INVENTION

To that end, the method according to the invention comprises the following steps:

a) taking a sagittal preoperative x-ray of the vertebral column of the patient to be treated, extending from the cervical vertebrae to the femoral heads;

b) on that x-ray, identifying:

the so-called "pelvic" parameters, i.e., the sacral slope, the pelvic version and the pelvic incidence, the lumbar lordosis, the position of the apical lumbar vertebra, i.e., that situated furthest forward on the x-ray, at least one of the following measurements:

the distance, called SVA, from the vertical of the posterior upper point of the plate of the first vertebra of the sacrum, called S1, to the vertical passing through the center of the 7th cervical vertebra;

the distance, called SFD, from the vertical of the posterior upper point of the plate of S1 to the vertical passing through the center of the femoral heads;

the angle, called T1/SPI, formed between the segment going from the center of the first dorsal vertebra, called T1, to the center of the femoral heads and the vertical to the center of T1, a cloud of points defining the curvature of the patient's vertebral column, including one point per vertebral level, positioned at the center of the upper plate of an affected vertebra, and a point defining the noted preoperative apex;

c) deducing, among predetermined vertebral column morphotypes and from the noted value of the sacral slope, the morphotype to which the treated vertebral column corresponds and deducing the desired postoperative apex point after performing the correction therefrom, and defining the vertebrae in which the anchor members for the vertebral rod to be anchored to the vertebrae will be implanted;

d) performing a wire modeling of the patient's vertebral column, for example using CAD software;

e) defining, from said pelvic parameters, a reference centered at the plate of S1, the origin point of which is the central point of that plate;

f) positioning the different points of said cloud of points, attached to each vertebra, in that reference, and drawing arcs step by step between the identified points, all of the arcs being tangent to each other and the arc extending from S1 being tangent to the straight line perpendicular to the plate of S1;

g) reading the values of the arc lengths;

h) simulating the correction to be applied to the lumbar segment to be treated as follows:

h1) drawing a straight line tangent to the desired postoperative apex point, moving that straight line to a vertical position such that the arc attached to that straight line is tangent to the desired postoperative apex point, the latter thus being repositioned so as to become the apex point of the modeled vertebral column segment, h2) defining, as co-radial to each other, the arcs situated below that apex point and defining as co-radial to each other the arcs situated above that same apex point, so as to obtain two different curvatures, one above that apex point and the other below the apex point, h3) defining the lumbar lordosis as being equal to plus or minus ten degrees of the pelvic incidence, and defining one of the following three values as desired:

SVA distance smaller than 5 cm;

SVA/SFD ratio comprised between −1.9 and +0.1; the value of this ratio is positive on the side of the vertical of the posterior upper point of the plate of S1 situated toward the femoral heads and is negative on the side of the vertical situated opposite the femoral heads;

T1/SPI angle comprised between −9° and 0°, that angle being negative on the side of the vertical at the center of T1 located toward the femoral heads;

h4) defining two arcs concentric to the two curvatures obtained during step h2 above, which are tangent to each other at the apex point, those arcs forming a curved segment representing the ideal curvature of the rod to be implanted in order to obtain the correction of the vertebral segment to be treated, h5) translating that curved segment away from the mean line of the vertebral column, over an evaluated mean distance going from the center of the vertebrae to the anchor points of the anchor members for anchoring the rod to the vertebrae of said vertebral segment to be treated, such that the position of said curve segment corresponds to the position the rod will assume once implanted;

i) defining the diameter of the rod to be implanted;

j) defining a two- or three-dimensional model of the rod, curved along said curve segment, and k) from a straight rod, producing the curvature of that rod according to said model.

Preferably, said predetermined vertebral column morphotypes comprise:

a so-called "type 1" morphotype, in which the apex (i.e., the forwardmost point of the vertebral column) is situated at the median plane of L5 (fifth lumbar vertebra), and the SS criterion corresponds to an angle smaller than 35°;

a so-called "type 2" morphotype, in which the apex is situated at the base of L4 (fourth lumbar vertebra), and the SS criterion corresponds to an angle smaller than 35°;

a so-called "type 3" morphotype, in which the apex is situated at the median plane of L4, and the SS criterion corresponds to an angle comprised between 35° and 45°;

a so-called "type 4" morphotype, in which the apex is situated at the base of L3 (third lumbar vertebra), and the SS criterion corresponds to an angle larger than 45°.

Preferably, the two- or three-dimensional modeling done in step j) consists of establishing a drawing or a plan of the rod to be produced.

Preferably, the curvature produced in step k) is done by cold bending.

Preferably, the method comprises, after step h5) or step i) or step j), the transfer of data relative to the rod to be produced to a service provider responsible for producing the curvature of the rod.

Thus, a practitioner, having determined the shape of the rod to be implanted using the method according to the invention, transfers the data relative to the rod to be produced to a service provider responsible for producing the curvature of the rod. Once that curvature is produced, the service provider will deliver the curved rod to the practitioner, who will be able to operate on the patient with his vertebral rod that is ready to be implanted.

The invention will be well understood, and other features and advantages thereof will appear, in reference to the appended diagrammatic drawing, showing, as a non-limiting example, different values used to carry out the method in question and different operations performed in the context of that implementation.

DESCRIPTION OF THE PREFERRED EMBODIMENTS

Figure 3:
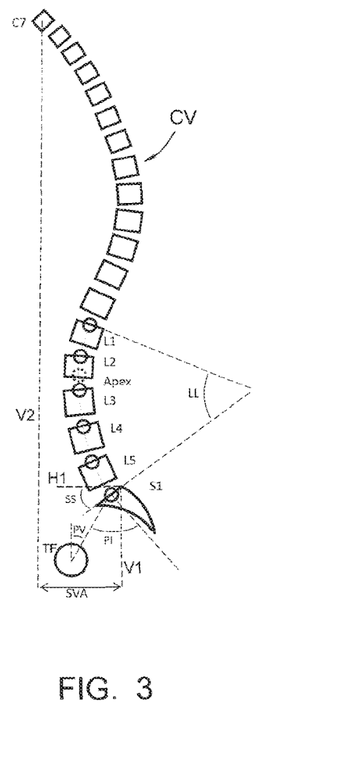
FIG. 3 is a very diagrammatic view of a vertebral column, on which the definition points of an SVA value used to implement the method according to the invention are shown.

FIG. 3 very diagrammatically shows a vertebral column CV, and includes the following information:

LL: vertebral segment to be treated;

L1, L2, L3, L4, L5, S1, C7: the first, second, third, fourth and fifth lumbar vertebrae, the first vertebra of the sacrum and the seventh cervical vertebra, respectively;

Apex: the forward most point of the vertebral column;

SS, PV, PI: the aforementioned pelvic criteria;

TF: the femoral heads, shown by a circle;

H1 and V1: the horizontal and vertical, respectively, at the posterior upper point of the plate of S1;

V2: the vertical passing through the center of the 7th cervical vertebra (C7).

Figure 4:
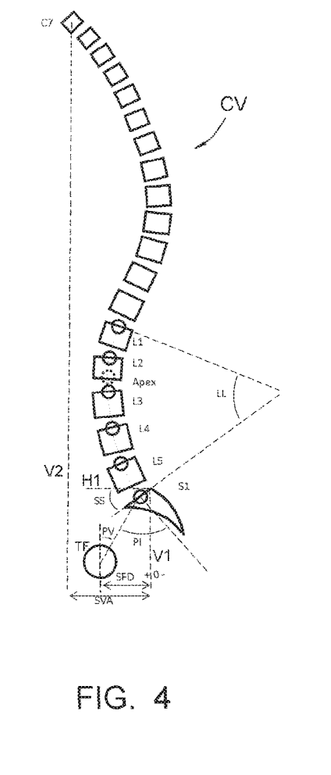
FIG. 4 is a view similar to FIG. 3, which shows the definition points of the SVA value and an SFD value, those two values being used to define a ratio employed to carry out the method according to the invention.

FIG. 4 also mentions a so-called "SFD" value, going from the vertical V1 to the vertical passing through the center of the femoral heads TF.

Figure 5:
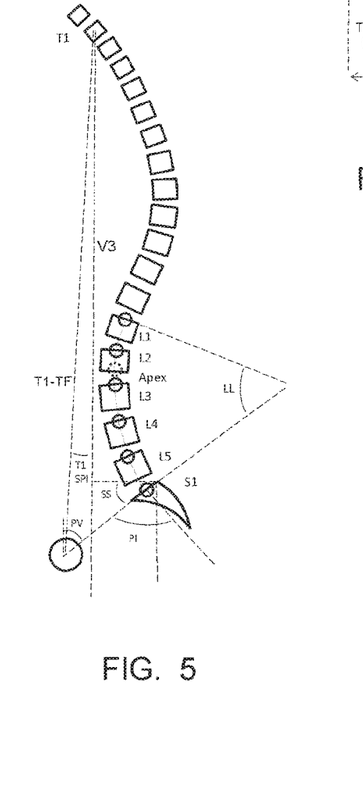
FIG. 5 is a view similar to FIG. 3, showing the definition points of a so-called T1/SPI value used to carry out the method according to the invention.

FIG. 5 also mentions a so-called "T1/SPI" value, which is the angle formed between the T1-TF segment going from the center of the first dorsal vertebra, called T1, to the center of the femoral heads TF and the vertical V3 to the center of T1.

The various steps of the method are illustrated in FIGS. 6 to 11 as follows.

Figure 6:
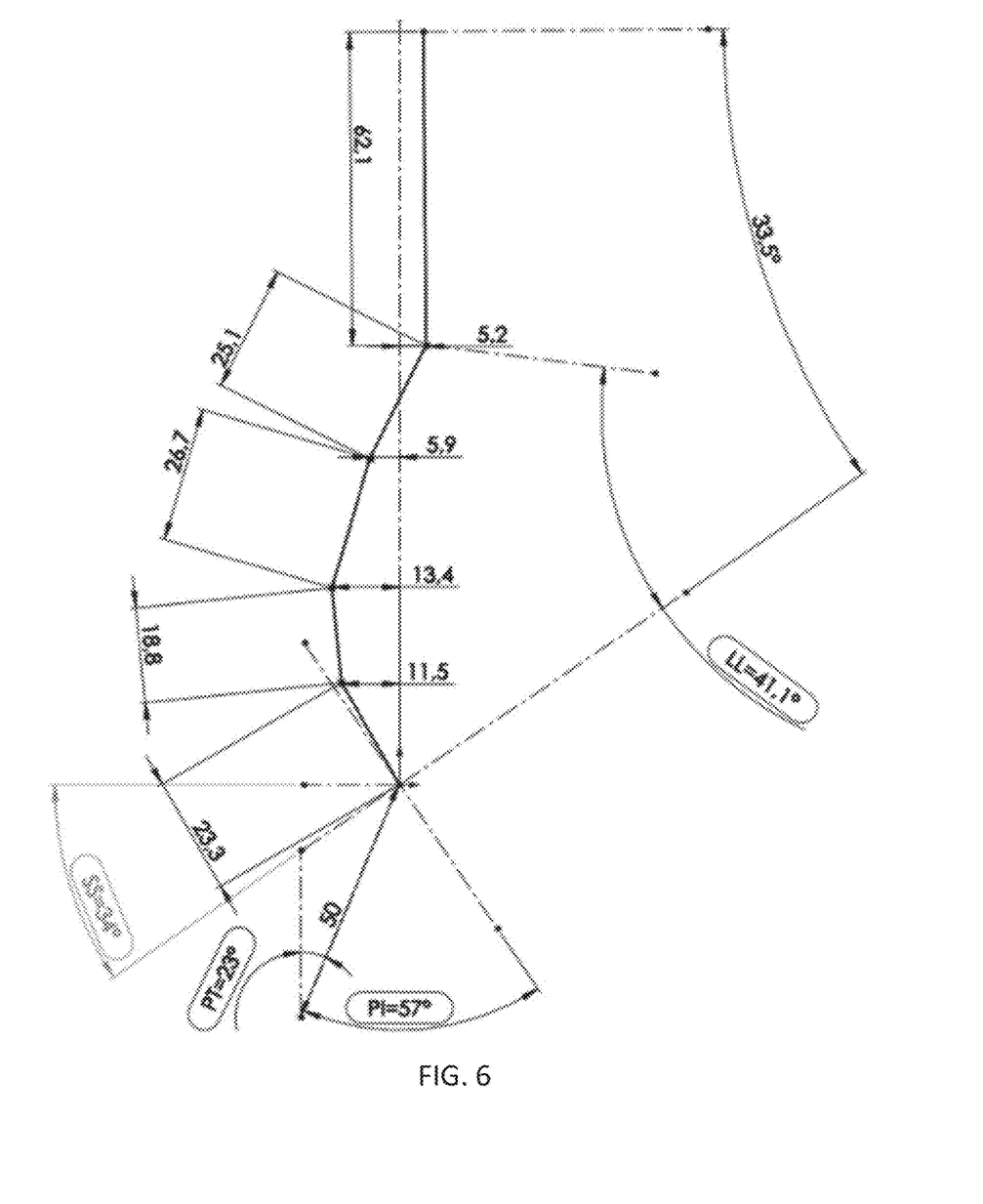
FIGS. 6 to 11 are very diagrammatic views of reference points, segments, arcs of circle and curves used during the different successive steps of this method.

FIG. 6: on a sagittal preoperative x-ray of the vertebral column of the patient to be treated, extending from the cervical vertebrae to the femoral heads, the following are identified:

the pelvic parameters,
the lumbar lordosis,
the position of the apical lumbar vertebra, i.e., that situated furthest forward on the x-ray,
as desired, the SVA distance only, or the SVA distance and the SFD distance,
a cloud of points defining the curvature of the patient's vertebral column, including one point per vertebral level, positioned at the center of the upper plate of an affected vertebra, and a point defining the noted preoperative apex.

The morphotype to which the treated vertebral column corresponds is deduced on the noted points, among the vertebral column morphotypes shown in FIGS. 2A to 2D, from the value of the noted sacral slope; the desired postoperative apex point after performing the correction is deduced therefrom; the vertebrae in which the anchoring members for the vertebral rod to be anchored to the vertebrae will be implanted are also defined in this step.

Figure 7:
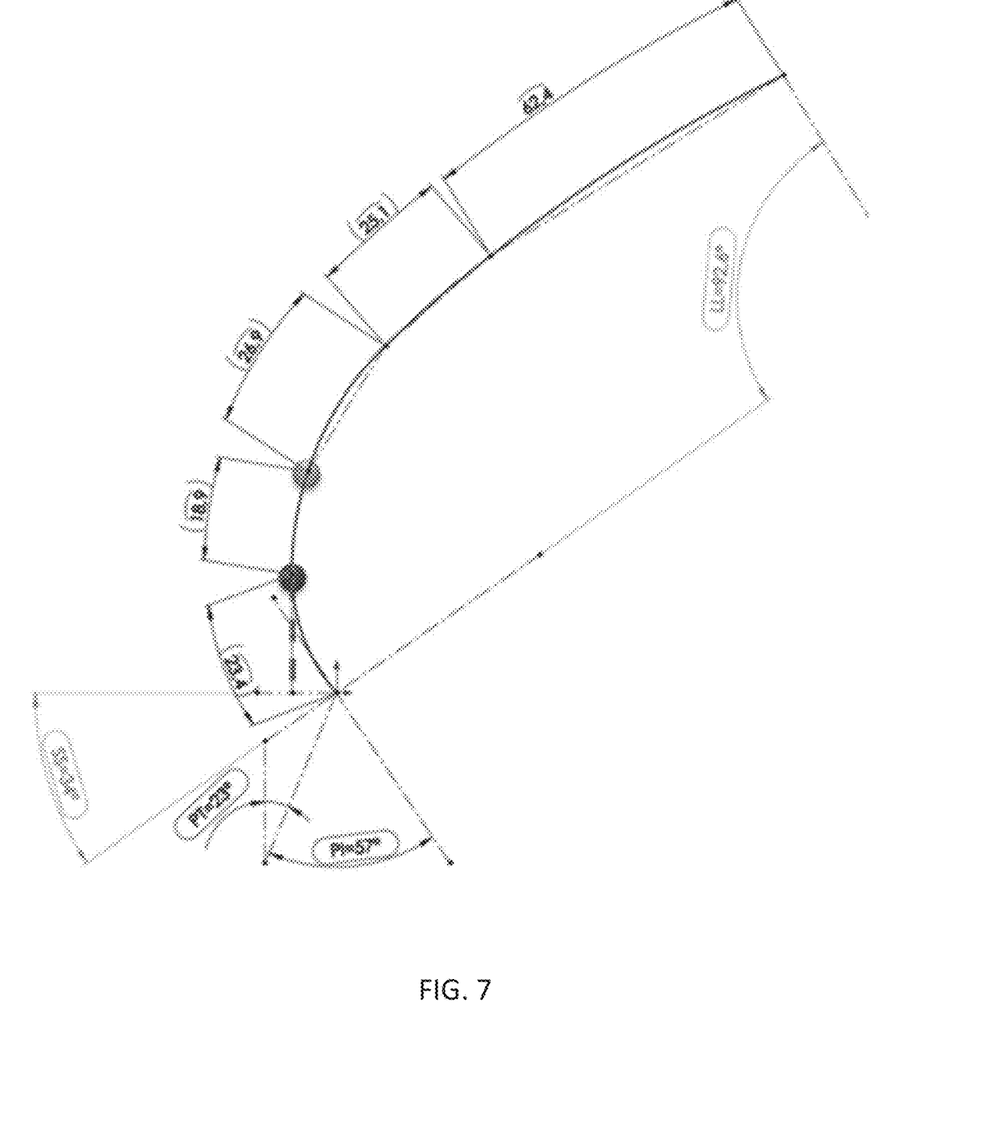
Figure 8:
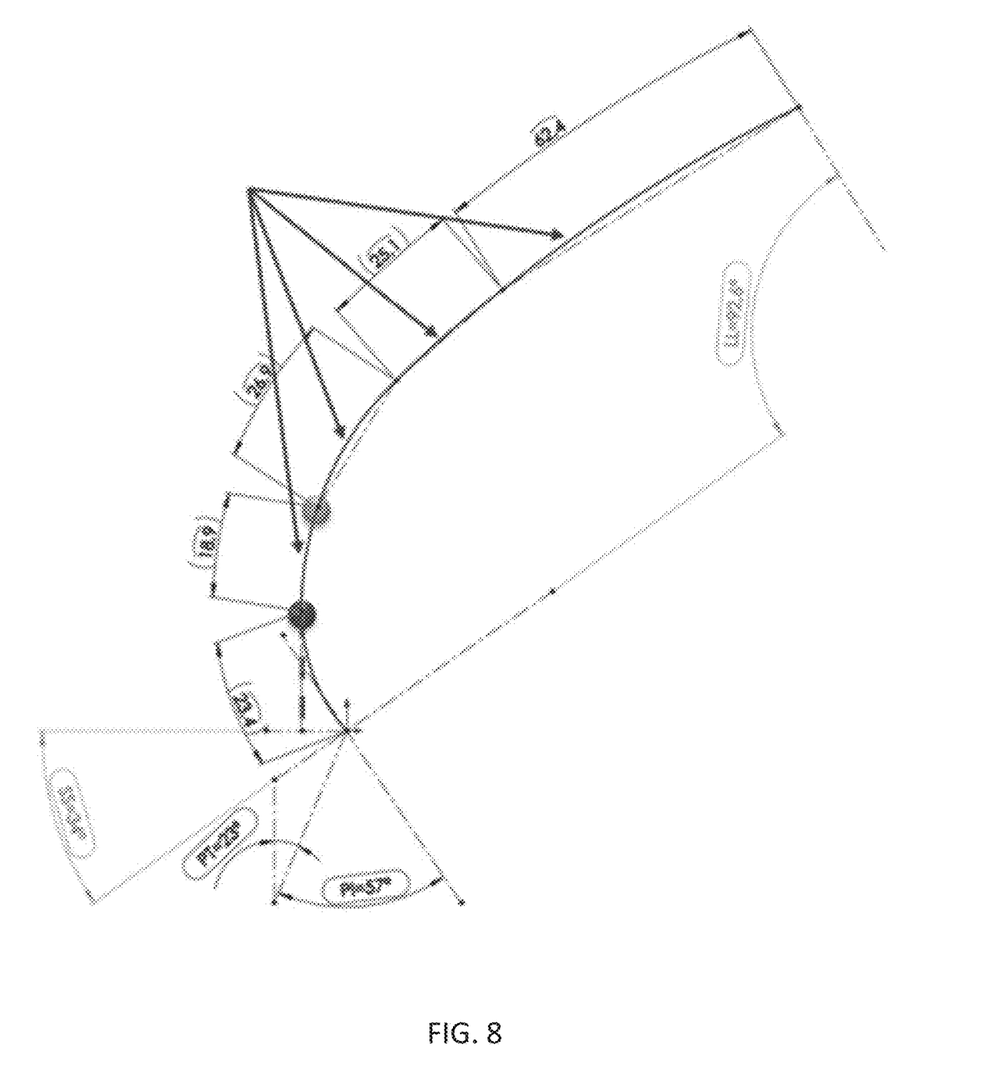
Figure 9:
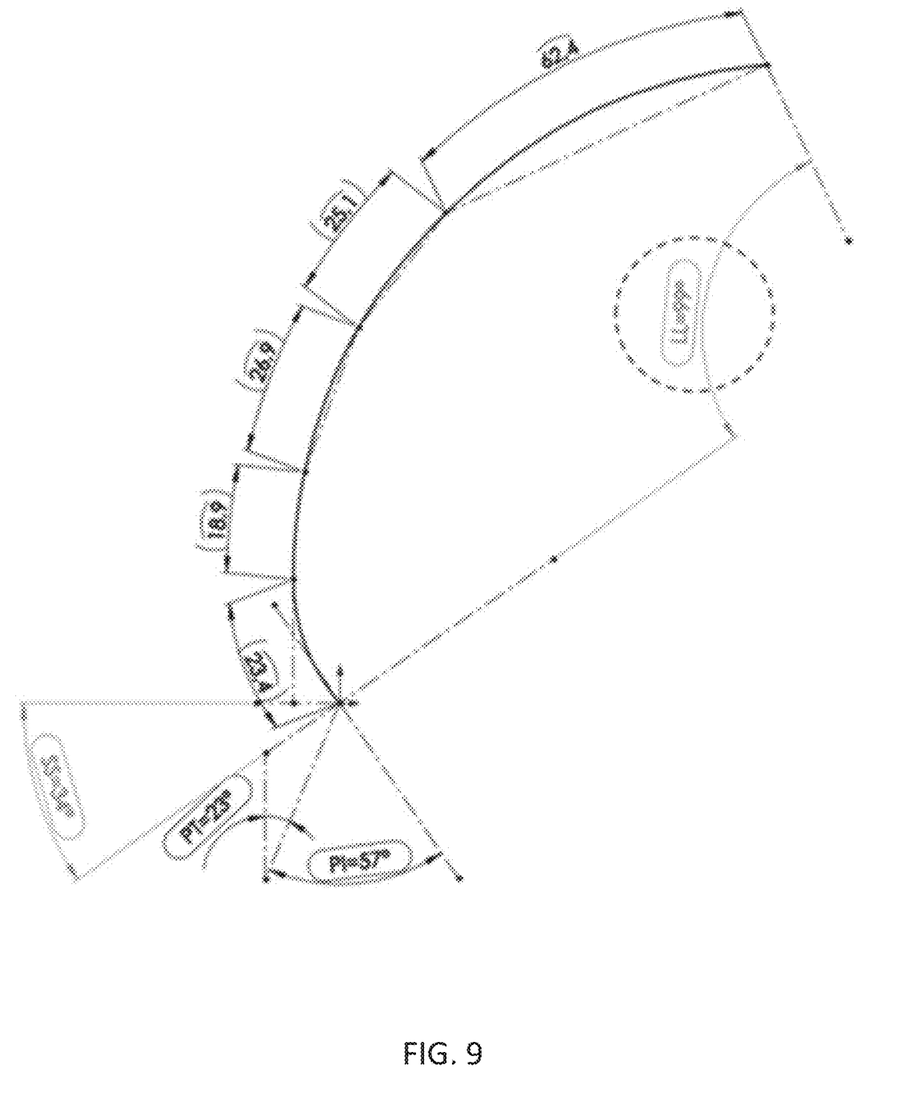
Figure 10:
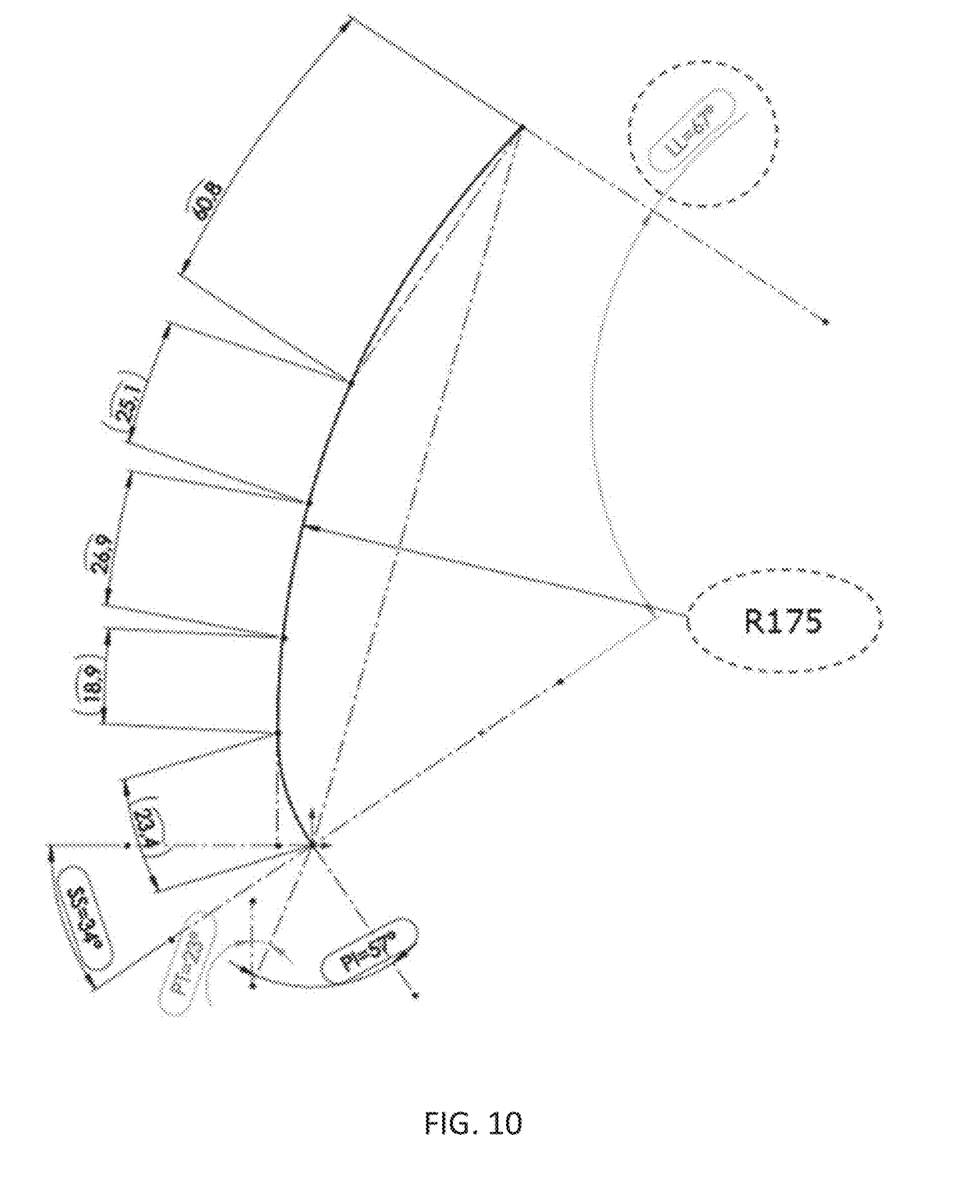

FIGS. 7 and 8: a wire model of the vertebral column of the patient is done, for example using CAD software;

FIG. 9: a reference centered at the plate of S1 is defined from said pelvic parameters, the origin point of that reference being the central point of that plate, then the different points of said cloud of points, attached to each vertebra, are positioned in that reference, and arcs between the identified points are drawn step by step, all of the arcs being tangent to each other and the arc extending from S1 being tangent to the straight line perpendicular to the plate of S1;

FIG. 10: the values of the arc lengths are read, and the correction to be applied to the lumbar segment to be treated is simulated as follows:

drawing a straight line tangent to the desired postoperative apex point, moving that straight line to a vertical position such that the arc attached to that straight line is tangent to that desired postoperative apex point, the latter thus being repositioned so as to become the apex point of the modeled vertebral column segment, defining, as co-radial to each other, the arcs situated below that apex point and defining, as co-radial to each other, the arcs situated above that same apex point, so as to obtain two different curvatures, one above that apex point and the other below that apex point, defining the lumbar lordosis as being equal to plus or minus ten degrees of the pelvic incidence, and defining, as desired, one of the three following values:

SVA distance smaller than 5 cm;
SVA/SFD ratio comprised between −1.9 and +0.1; the value of this ratio is positive on the side of the vertical V1 situated toward the femoral heads TF and is negative on the side of that vertical V1 situated opposite the femoral heads TF;

T1/SPI angle comprised between −9° and 0°; this angle is negative on the side of the vertical V3 at the center of T1 located toward the femoral heads TF;

defining two arcs concentric to the two curvatures obtained in the above step, which are tangent to each other at the apex point, those arcs forming a curved segment SC representing the ideal curvature of the rod to be implanted in order to obtain the correction of the vertebral segment to be treated.

Figure 11:
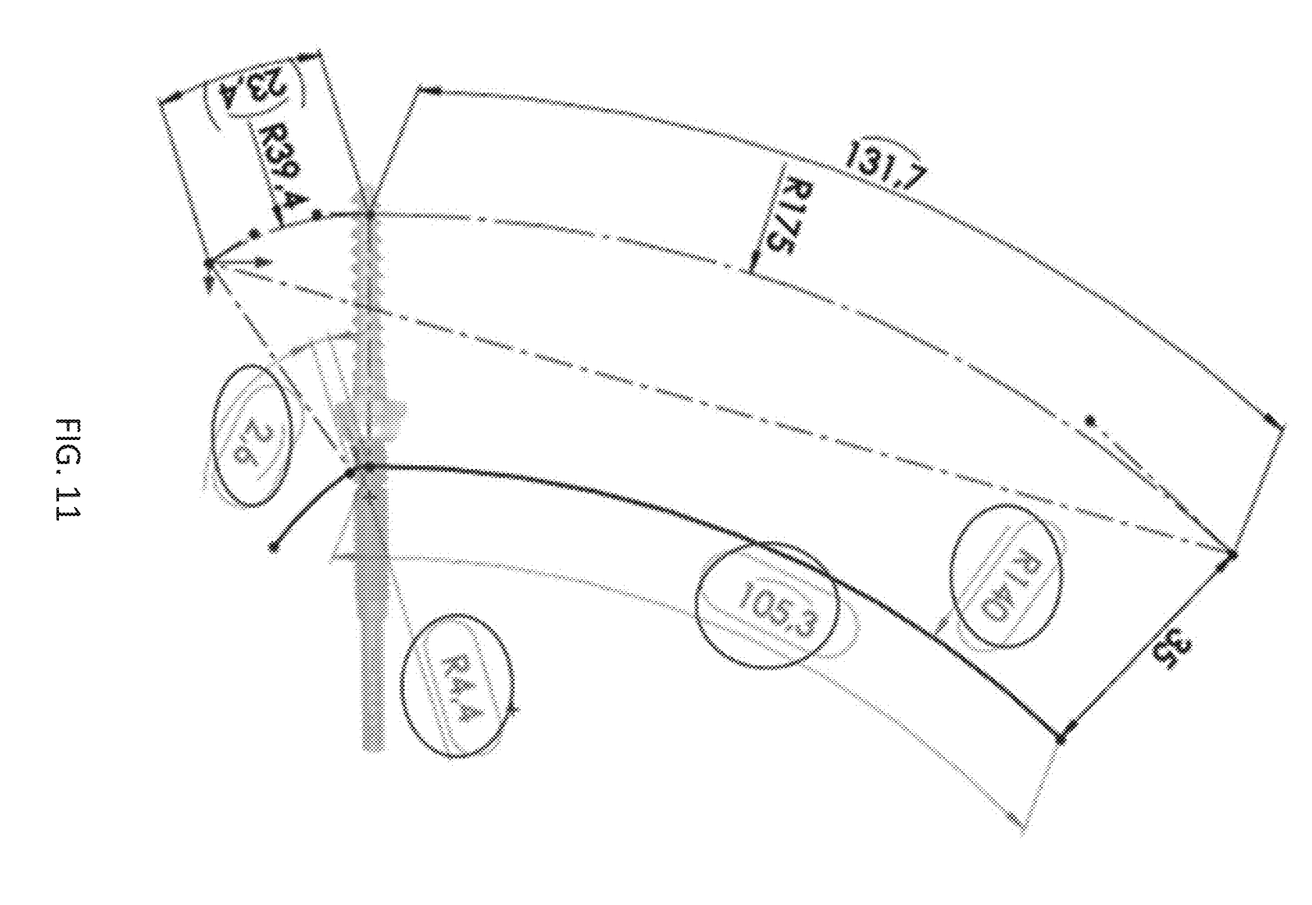

FIG. 11: the curved segment SC is translated away from the mean line of the vertebral column, over an evaluated mean distance going from the center of the vertebrae to the anchoring points of the anchoring members OA (FIG. 10, it is a pedicle screw) for anchoring the rod to the vertebrae of said vertebral segment to be treated, such that the position of said curve segment SC corresponds to the position that the rod will assume once implanted; the diameter of the rod to be implanted being defined, a two- or three-dimensional model of that rod is then established, curved along said arcs.

Figure 12:
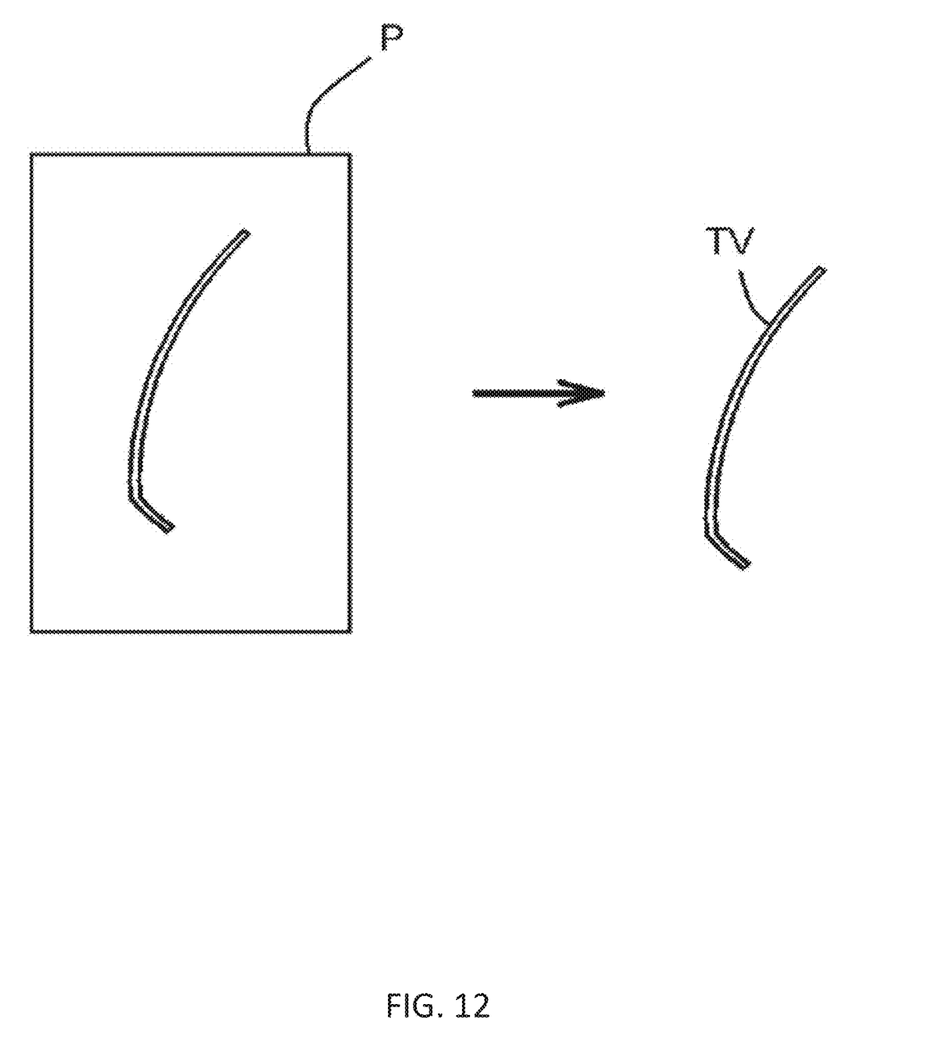
FIG. 12 is, on the left side of that figure, a view of a drawing or plan P of the curved vertebral rod to be obtained, the shape of which has been defined by the preceding steps of the method and, on the right side of that figure, a view of the curved vertebral rod TV, obtained from that drawing P.

FIG. 12: a drawing or plan P is established from that model, then the vertebral rod TV to be obtained is arranged from that drawing P, in particular by cold bending.

The method according to the invention thus has the decisive advantage of making it possible to produce the ideal curvature of a rod for vertebral osteosynthesis material designed to support a patient's vertebral column.

What is claimed is:

1. A method for producing a curvature of a rod of vertebral osteosynthesis material designed to support a vertebral column of a patient, the method comprising:

taking a sagittal preoperative x-ray of a vertebral column of a patient to be treated;

identifying on the sagittal preoperative x-ray:
　one or more pelvic parameters;
　a lumbar lordosis;
　a position of an apical lumbar vertebra;
　at least one of the following measurements:
　　a SVA distance from a vertical of a posterior upper point of a plate of a first vertebra of a sacrum (S1) to a vertical passing through a center of a seventh cervical vertebra;
　　a SFD distance from the vertical of the posterior upper point of the plate of S1 to a vertical passing through a center of a femoral head; or
　　a T1/SPI angle formed between a segment going from a center of a first dorsal vertebra (T1) to the center of the femoral head and a vertical line extending from the center of T1; and
　a plurality of points defining a preoperative curvature of the vertebral column of the patient, wherein the plurality of points comprises one point per vertebral level;

deducing, among predetermined vertebral column morphotypes, a morphotype to which the vertebral column corresponds, deducing a desired postoperative apex point, and defining the vertebrae in which one or more anchor members for a vertebral rod to be anchored to the vertebrae will be implanted;

defining, from the one or more pelvic parameters, a reference centered at the plate of S1;

adjusting a position of one or more of the plurality of points and drawing a plurality of arcs through the one or more of the plurality of points, wherein at least one of the plurality of arcs is tangent to another one of the plurality of arcs, and wherein an arc extending from S1 is tangent to a straight line perpendicular to the plate of S1;

determining values of lengths of the plurality of arcs;

simulating a correction to be applied to a lumbar segment to be treated, wherein simulating the correction comprises:

drawing a straight line tangent to the desired postoperative apex point, moving the straight line to a vertical position such that an arc attached to the straight line is tangent to the desired postoperative apex point, the desired postoperative apex point being repositioned so as to become an apex point of the modeled vertebral column segment;

adjusting a first subset of the plurality of arcs situated below the apex point to make the first subset of the plurality of arcs co-radial to each other and adjusting a second subset of the plurality of arcs situated above the apex point to make the second subset of the plurality of arcs co-radial to each other, and obtain a first curvature above the apex point and a second curvature below the apex point;

defining the lumbar lordosis as being within ten degrees of a pelvic incidence, and defining one or more of:
an SVA distance smaller than 5 cm;
an SVA/SFD ratio between −1.9 and +0.1, wherein the SVA/SFD ratio is positive on a side of the vertical of the posterior upper point of the plate of S1 situated toward the femoral head, and wherein the SVA/SFD ratio is negative on a side of the vertical situated opposite the femoral head; or
a T1/SPI angle between −9° and 0°, wherein the T1/SPI angle is negative on a side of the vertical at the center of T1 located toward the femoral head;

defining a first concentric arc and a second concentric arc, wherein the first concentric arc is concentric to the first curvature above the apex point, and wherein the second concentric arc is concentric to the second curvature below the apex point, wherein the first concentric arc and the second concentric arc form a curved segment representing a desired curvature of the rod to be implanted in order to obtain the correction of the vertebral column to be treated; and translating the curved segment away from a mean line of the vertebral column, over a mean of distances between a center of the vertebrae to each of the one or more anchor points of the anchor members for anchoring the rod to the vertebrae of the vertebral column to be treated, such that a position of the curved segment corresponds to a position the rod will assume once implanted;

defining a diameter of the rod to be implanted;

defining a two- or three-dimensional model of the rod, curved along the curved segment;

transmitting data relating to the desired curvature of the rod to a production unit; and from a straight rod, physically producing the curvature of the rod by the production unit according to the model.

2. The method of claim 1, wherein the predetermined vertebral column morphotypes comprise one or more of:
a type 1 morphotype, in which a forwardmost point of the vertebral column is situated at a median plane of L5, and an SS criterion corresponds to an angle smaller than 35°;

a type 2 morphotype, in which the forwardmost point of the vertebral column is situated at a base of L4, and the SS criterion corresponds to an angle smaller than 35°;

a type 3 morphotype, in which the forwardmost point of the vertebral column is situated at a median plane of L4, and the SS criterion corresponds to an angle between 35° and 45°; or a type 4 morphotype, in which the forwardmost point of the vertebral column is situated at a base of L3, and the SS criterion corresponds to an angle larger than 45°.

3. The method of claim 1, wherein defining the two- or three-dimensional modeling comprises establishing a drawing or plan of the rod to be produced.

4. The method of claim 1, wherein the curvature of the rod is physically produced by cold bending.

5. The method of claim 1, wherein data relating to the desired curvature of the rod is transmitted to a service provider that operates the production unit for physically producing the curvature of the rod.

6. The method of claim 1, wherein the one or more pelvic parameters comprises one or more of a sacral slope, a pelvic version, or a pelvic incidence.

7. The method of claim 1, wherein the apical lumbar vertebra is situated furthest forward on the sagittal preoperative x-ray.

8. The method of claim 1, wherein the sagittal preoperative x-ray of the vertebral column extends from the cervical vertebrae to the femoral head.

9. The method of claim 1, wherein the two- or three-dimensional model of the rod is defined using CAD software.

10. A system for producing a desired curvature of a rod of vertebral osteosynthesis material designed to support a vertebral column of a patient, the system comprising:

an interface configured to analyze a sagittal preoperative x-ray of a vertebral column of a patient to be treated, wherein the sagittal preoperative x-ray is analyzed by identifying on the sagittal preoperative x-ray:
one or more pelvic parameters;
a lumbar lordosis;
a position of an apical lumbar vertebra;
at least one of the following measurements:
a SVA distance-from a vertical of a posterior upper point of a plate of a first vertebra of a sacrum (S1) to a vertical passing through a center of a seventh cervical vertebra;
a SFD distance from the vertical of the posterior upper point of the plate of S1 to a vertical passing through a center of a femoral head; or
a T1/SPI angle formed between a segment going from a center of a first dorsal vertebra (T1) to the center of the femoral head and a vertical line extending from the center of T1; and
a plurality of points defining a preoperative curvature of the vertebral column of the patient, wherein the plurality of points comprises one point per vertebral level;

the interface further configured to determine, among predetermined vertebral column morphotypes, a morphotype to which the vertebral column corresponds, determine a desired postoperative apex point, and defining the vertebrae in which one or more anchor members for a vertebral rod to be anchored to the vertebrae will be implanted;

the interface further configured to define, from the one or more pelvic parameters, a reference centered at the plate of S1;

the interface further configured to adjust a position of one or more of the plurality of points and draw a plurality of arcs through the one or more of the plurality of points, wherein at least one of the plurality of arcs is tangent to another one of the plurality of arcs, and wherein an arc extending from S1 is tangent to a straight line perpendicular to the plate of S1;

the interface further configured to determine values of lengths of the plurality of arcs;

the interface further configured to simulate a correction to be applied to a lumbar segment to be treated, wherein simulating the correction comprises:

drawing a straight line tangent to the desired postoperative apex point, moving the straight line to a vertical position such that an arc attached to the straight line is tangent to the desired postoperative apex point, the desired postoperative apex point being repositioned so as to become an apex point of the modeled vertebral column segment;

adjusting a first subset of the plurality of arcs situated below the apex point to make the first subset of the plurality of arcs co-radial to each other and adjusting a second subset of the plurality of arcs situated above the apex point to make the second subset of the plurality of arcs co-radial to each other, and obtain a first curvature above the apex point and second curvature below the apex point;

defining the lumbar lordosis as being within ten degrees of a pelvic incidence, and defining one or more of:
an SVA distance smaller than 5 cm;
an SVA/SFD ratio between −1.9 and +0.1, wherein the SVA/SFD ratio is positive on a side of the vertical of the posterior upper point of the plate of S1 situated toward the femoral head, and wherein the SVA/SFD ratio is negative on a side of the vertical situated opposite the femoral head; or
a T1/SPI angle between −9° and 0°, wherein the T1/SPI angle is negative on a side of the vertical at the center of T1 located toward the femoral head;

defining a first concentric arc and a second concentric arc, wherein the first concentric arc is concentric to the first curvature above the apex point, and wherein the second concentric arc is concentric to the second curvature below the apex point, wherein the first concentric arc and the second concentric arc form a curved segment representing a desired curvature of the rod to be implanted in order to obtain the correction of the vertebral column to be treated; and translating the curved segment away from a mean line of the vertebral column, over a mean of distances between a center of the vertebrae to each of the one or more anchor points of the anchor members for anchoring the rod to the vertebrae of the vertebral column to be treated, such that a position of the curved segment corresponds to a position the rod will assume once implanted;

the interface further configured to define a diameter of the rod to be implanted;

the interface further configured to define a two- or three-dimensional model of the rod, curved along the curved segment;

the interface further configured to transmit data relating to the desired curvature of the rod to a production unit; and the production unit configured to physically produce, from a straight rod, the curvature of the rod according to the model, wherein the interface comprises a computer processor and an electronic storage medium.

11. The system of claim 10, wherein the predetermined vertebral column morphotypes comprise one or more of:
a type 1 morphotype, in which a forwardmost point of the vertebral column is situated at a median plane of L5, and an SS criterion corresponds to an angle smaller than 35°;
a type 2 morphotype, in which the forwardmost point of the vertebral column is situated at a base of L4, and the SS criterion corresponds to an angle smaller than 35°;
a type 3 morphotype, in which the forwardmost point of the vertebral column is situated at a median plane of L4, and the SS criterion corresponds to an angle between 35° and 45°; or
a type 4 morphotype, in which the forwardmost point of the vertebral column is situated at a base of L3, and the SS criterion corresponds to an angle larger than 45°.

12. The system of claim 10, wherein the two- or three-dimensional modeling is defined by establishing a drawing or plan of the rod to be produced.

13. The system of claim 10, wherein the curvature of the rod is physically produced by cold bending.

14. The system of claim 10, wherein the one or more pelvic parameters comprises one or more of a sacral slope, a pelvic version, or a pelvic incidence.

15. The system of claim 10, wherein the apical lumbar vertebra is situated furthest forward on the sagittal preoperative x-ray.

16. The system of claim 10, wherein the sagittal preoperative x-ray of the vertebral column extends from the cervical vertebrae to the femoral head.

17. The system of claim 10, wherein the two- or three-dimensional model of the rod is defined using CAD software.

* * * * *